(12) United States Patent
Cox et al.

(10) Patent No.: US 6,728,478 B2
(45) Date of Patent: Apr. 27, 2004

(54) HEATED CHEMICAL DELIVERY SYSTEM

(75) Inventors: Robert G. Cox, Goshen, IN (US); Jeremiah M. Lewis, Leesburg, IN (US)

(73) Assignee: Dekko Heating Technologies, Inc., North Webster, IN (US)

( * ) Notice: Subject to any disclaimer, the term of this patent is extended or adjusted under 35 U.S.C. 154(b) by 0 days.

(21) Appl. No.: 10/371,726

(22) Filed: Feb. 20, 2003

(65) Prior Publication Data

US 2003/0156830 A1 Aug. 21, 2003

Related U.S. Application Data

(60) Provisional application No. 60/358,679, filed on Feb. 21, 2002.

(51) Int. Cl.[7] .............................................. A61M 16/00
(52) U.S. Cl. ........................ 392/390; 392/392; 392/403; 222/146.1
(58) Field of Search ........................ 392/386, 390–394, 392/399, 403; 222/129, 146.1, 146.2, 146.5

(56) References Cited

U.S. PATENT DOCUMENTS

| | | | | |
|---|---|---|---|---|
| 3,908,905 A | * | 9/1975 | Von Philip et al. | ........... 239/55 |
| 4,849,606 A | * | 7/1989 | Martens et al. | ............. 392/390 |
| 5,394,506 A | * | 2/1995 | Stein et al. | ................. 392/395 |
| D359,346 S | * | 6/1995 | Martin | ....................... D23/366 |
| 6,123,935 A | * | 9/2000 | Wefler et al. | .............. 424/76.1 |

* cited by examiner

Primary Examiner—Edward K. Look
Assistant Examiner—Thor Campbell
(74) Attorney, Agent, or Firm—Taylor & Aust, P.C.

(57) ABSTRACT

A heated chemical delivery system with an electrical plug-in, a heater electrically connected to the electrical plug-in and a housing connected to both the electrical plug-in and the heater. The housing includes a plurality of sides and a plurality of side openings with each side opening associated with a respective side. At least two of the side openings have different cross-sectional configurations corresponding to different chemical packets to be received therein.

15 Claims, 3 Drawing Sheets

HEATED CHEMICAL DELIVERY SYSTEM

Cross Reference to Related Applications

This is a non-provisional application based upon U.S. provisional patent application serial No. 60/358,679, entitled "HEATED CHEMICAL DELIVERY SYSTEM", filed Feb. 21, 2002.

BACKGROUND OF THE INVENTION

1. Field of the Invention

The present invention relates to a heated chemical delivery system, and, more particularly, to a heated chemical delivery systems using a replaceable or refillable chemical packet.

2. Description of the Related Art

Electrically heated air fresheners are used for deodorizing and scenting the ambient air in enclosed spaces such as in a home or office. These devices utilize a fragrance element that is heated to motivate the escape of a deodorant or scent into the surrounding atmosphere. This is accomplished by increasing the temperature of the concentrated fragrance element material to a sufficient level to vaporize the concentrated form and dissipate the fragrance into the ambient.

An air freshener unit that is electrically actuated may be plugged into a wall outlet to power a small heating element within the unit. The heating element is proximate to a cavity or receptacle in which a thermally activated substance is stored. If the air freshener unit is a reusable unit, the thermally activated substance is typically a refillable or replaceable cartridge that is activated by the heat. Over time, a new supply of air freshener substance is required which typically will require some disassembly of the unit. Further, an air freshener unit is limited to one size of packet or cartridge.

What is needed in the art is a heated chemical delivery system device and method that allows for easy and quick replacement of a replaceable or refillable packet and that can accommodate different sizes of packets.

SUMMARY OF THE INVENTION

The present invention provides a heated chemical delivery system with at least one side opening that allows for easy replacement of chemical packets.

The invention comprises, in one form thereof, a heated chemical delivery system with an electrical plug-in, a heater electrically connected to the electrical plug-in and a housing connected to both the electrical plug-in and the heater. The housing includes a plurality of sides and a plurality of side openings with each side opening associated with a respective side. At least two of the side openings have different cross-sectional configurations corresponding to different chemical packets to be received therein.

An advantage of the present invention is a heated chemical delivery system device and method that allows for easy and quick replacement of a replaceable or refillable packet.

Another advantage of the present invention is a heated chemical delivery system device and method that can accommodate different size chemical packets.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
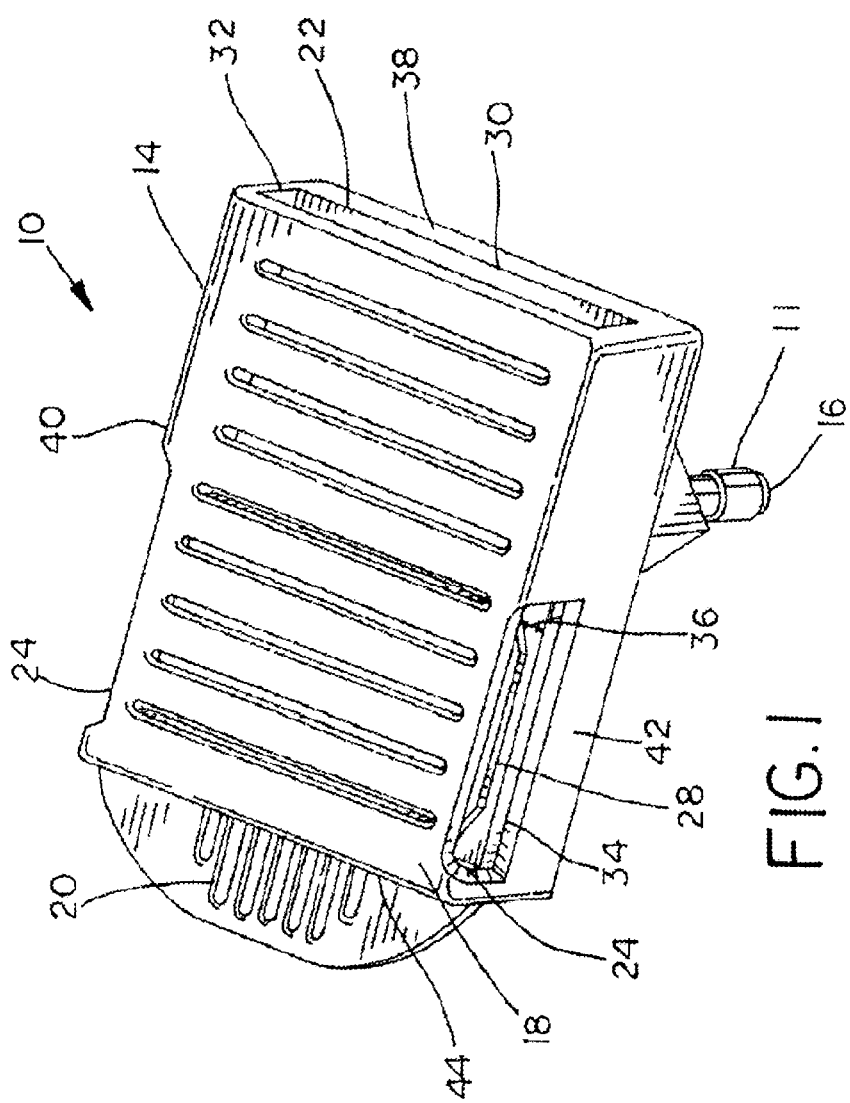
FIG. 1 is a perspective view of an embodiment of the present invention showing a small chemical packet installed.

Referring now to the drawings, there is shown an embodiment of a heated chemical deliver system 10 of the present invention. Chemical delivery system 10 generally includes an electrical plug-in 11, heater 12 and housing 14.

Electrical plug-in 10 includes male prongs 16 of the European style. While, chemical delivery system 10 is shown with a plug-in corresponding to a European style plug-in, alternatively, other style plug-ins can be used. Electrical plug-in 10 can be connected to a source of electrical power (not shown) at male prongs 16 to activate heated chemical deliver system 10.

Heater 12 electrically connects to electrical plug-in 11. Heater 12 typically includes a resistive heater element which generates heat when electrical plug-in 11 is connected to a source of electrical power (not shown). Heater 12 can include an indicator light to indicate when heater 12 is connected to a source of electrical power, a fuse for overcurrent circuit protection of heater 12, a thermostat for overtemperature protection of heater 12 and the like. The heater element can be a positive temperature coefficient (PTC) heater. Heater elements other than PTC or resistive heater elements can be used.

Figure 2:
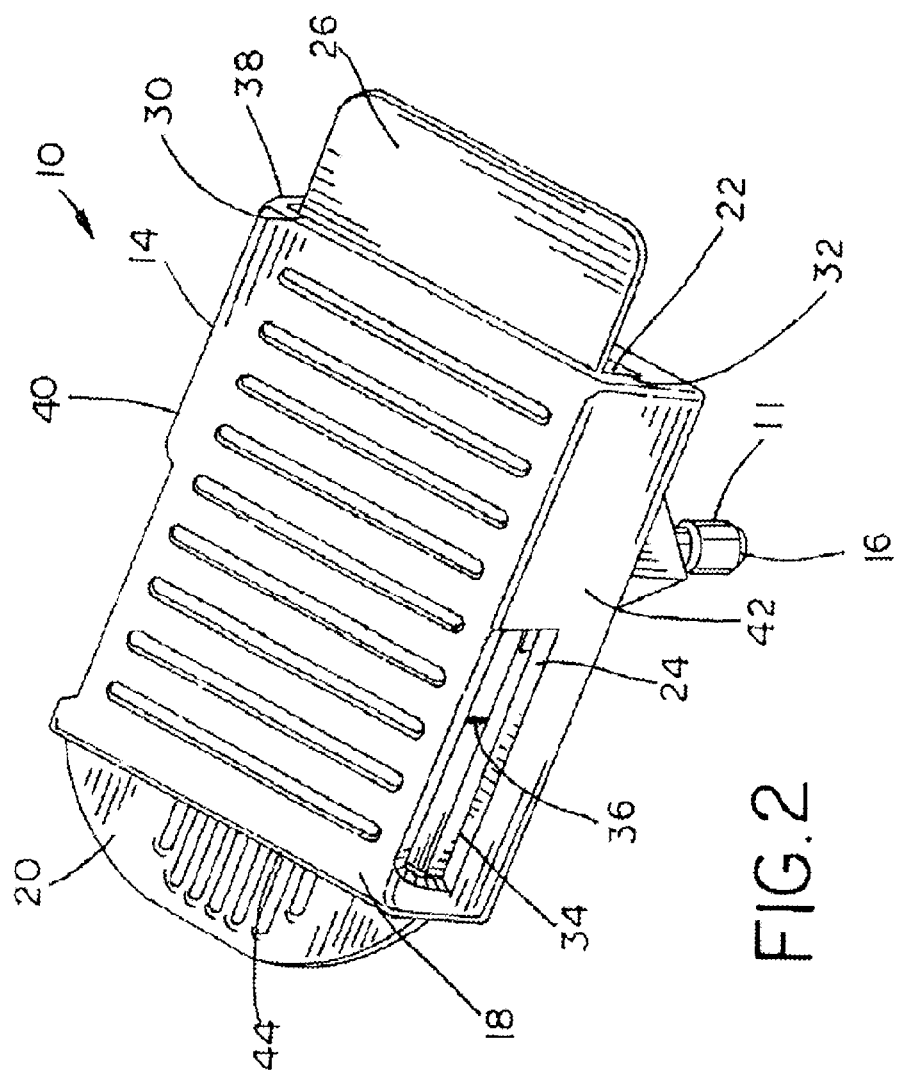
FIG. 2 is a perspective view of FIG. 1 showing a large chemical packet partially installed.
Figure 3:
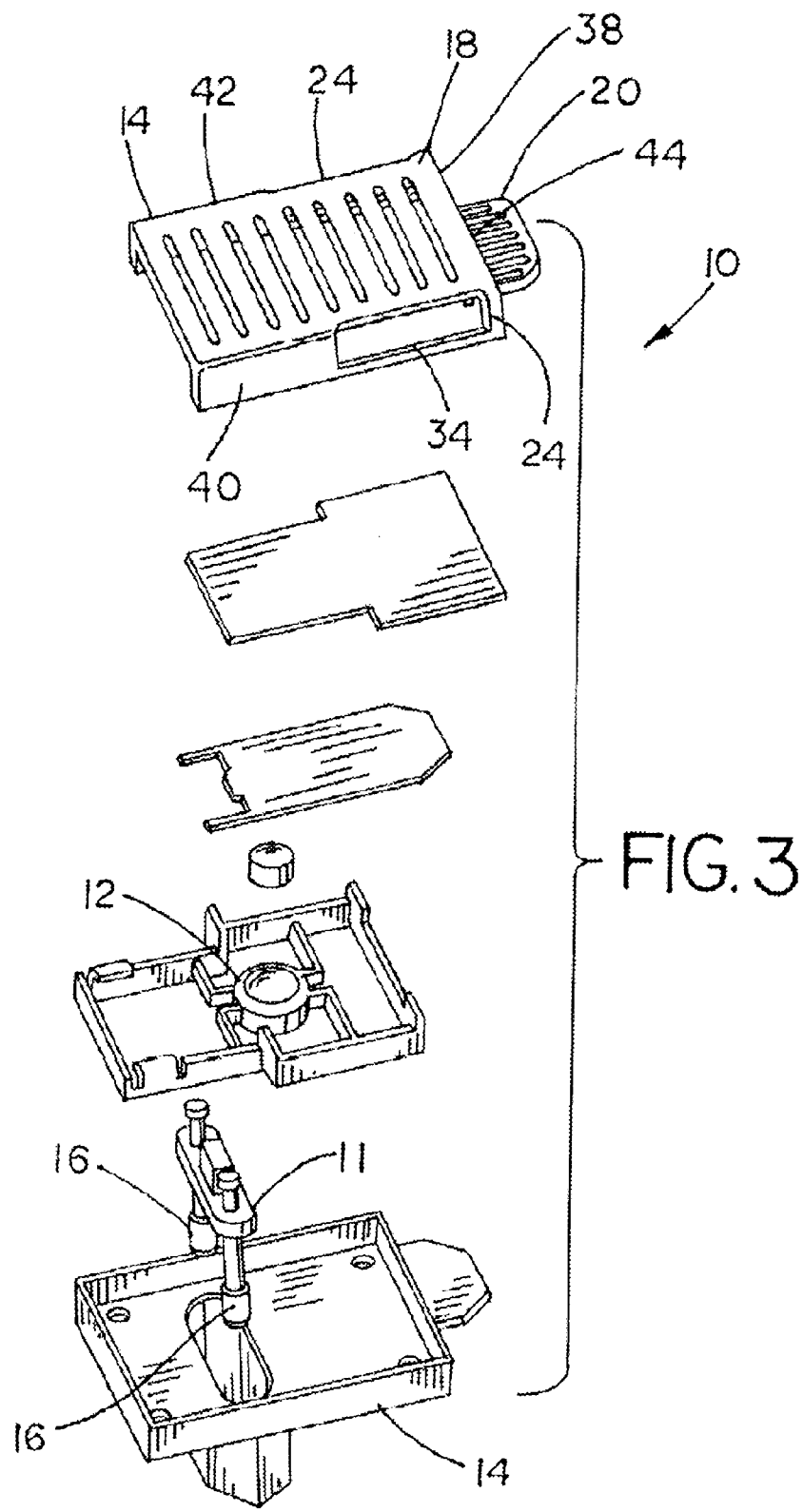
FIG. 3 is an exploded view of the heated chemical delivery system of FIG. 1.

Housing 14 includes vented cover 18 and night light 20 incorporated within housing 14. Night light 20 is electrically connected to electrical plug-in 11. Night light 20 can be incandescent, electroluminescent, LED or other suitable light sources. Vented cover 18 includes sides 38, 40, 42 and 44. Side 38 includes large side opening 22 and sides 40, 42 includes a pair of smaller side openings 24, each opening is in proximity to heater 12, such as a resistive heater, etc. within housing 14. Large side opening 22 and small side openings 24 are each sized and configured to receive a corresponding chemical packet 26, 28, respectively therein. In FIG. 1, a small packet 28 is shown within small side openings 24. In FIG. 2, a large packet 26 is shown partially within large side opening 22. Small packet 28 and/or large packet 26 can be of any suitable type which allows delivery into the ambient environment, such as fragrances, insecticides, air fresheners, aromatherapy chemicals, antimold compounds, anti-mildew compounds and other chemicals.

Large side opening 22 includes large side opening width 30 and large side opening depth 32. Small side openings 24 include small side opening width 34 and small side opening depth 36. Large side opening width 30 can be larger than small side opening width 34, therefore allowing for a wider large packet 26. Small side opening depth 36 can be larger than large side opening depth 32, therefore allowing for a thicker small packet 28. If these two comparative conditions are used in the design of the present invention, large packet 26 including a larger width can only be inserted within large side opening 22 and small packet 28 including a larger thichness can only be inserted within small side openings 24.

Alternatively, heated chemical deliver system 10 can include a plug or stop (not shown) to block one of small side openings 24 to ensure proper location of small packet 28 within housing 14. Also alternatively, small packet 28 can include a tab (not shown) at one end of small packet 28 to restrict small packet 28 from sliding past a proper registration location. A further alternative of heated chemical deliver system 10 includes a single small side opening 24.

In use, heated chemical delivery system 10 is connected to a source of electrical power (not shown) and a chemical packet 26 or 28 is slid into a selected side opening 22 or 24 with a corresponding cross-sectional configuration. Heater 12 heats a chemical in chemical packet 26 or 28 and at least a portion of the chemical is volatilized thereby releasing the chemical into the ambient.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. heated chemical delivery system, comprising:
   an electrical plug-in;
   a heater electrically connected to said electrical plug-in; and
   a housing connected to both said electrical plug-in and said heater, said housing including a plurality of sides and a plurality of side openings, each said side opening associated with a respective said side, at least two of said side openings having different cross-sectional configurations corresponding to different chemical packets to be received therein.

2. The heated chemical delivery system of claim 1, wherein said housing includes a first side and a second side, said at least one side opening includes a first side opening in said first side and a second side opening in said second side.

3. The heated chemical delivery system of claim 2, wherein said housing includes a third side approximately parallel to said second side, said at least one side opening including a third side opening in said third side.

4. The heated chemical delivery system of claim 2, wherein said first side opening includes a first side opening width, said second side opening includes a second side opening width, said first side opening width greater than said second side opening width.

5. The heated chemical delivery system of claim 2, wherein said first side opening includes a first side opening depth, said second side opening includes a second side opening depth, said second side opening depth greater than said first side opening depth.

6. The heated chemical delivery system of claim 1, further including a night light electrically connected to said plug-in.

7. The heated chemical delivery system of claim 6, wherein said night light is one of incandescent, electroluminescent and LED.

8. A heated chemical delivery system, comprising:
   an electrical plug-in;
   a heater electrically connected to said electrical plug-in;
   a housing connected to both said electrical plug-in and said heater, said housing including a plurality of sides and a plurality of side openings, each said side opening associated with a respective said side, at least two of said side openings having different cross-sectional configurations corresponding to different chemical packets to be received therein; and
   a chemical packet located in said housing and accessible through at least one said side opening.

9. The heated chemical delivery system of claim 8, wherein said housing includes a first side and a second side, said at least one side opening includes a first side opening in said first side and a second side opening in said second side.

10. The heated chemical delivery system of claim 9, wherein said housing includes a third side approximately parallel to said second side, said at least one side opening including a third side opening in said third side.

11. The heated chemical delivery system of claim 9, wherein said first side opening includes a first side opening width, said second side opening includes a second side opening width, said first side opening width greater than said second side opening width.

12. The heated chemical delivery system of claim 9, wherein said first side opening includes a first side opening depth, said second side opening includes a second side opening depth, said second side opening depth greater than said first side opening depth.

13. The heated chemical delivery system of claim 8, further including a night light electrically connected to said plug-in.

14. The heated chemical delivery system of claim 13, wherein said night light is one of incandescent, electroluminescent and LED.

15. A method of dispensing a chemical, comprising the steps of:
   connecting a heated chemical delivery system to a source of electrical power, said heated chemical delivery system including a plurality of sides and a plurality of side openings, each said side opening associated with a respective said side, at least two of said side openings having different cross-sectional configurations corresponding to different chemical packets to be received therein;
   sliding a chemical packet into a selected one of said plurality of side openings;
   heating a chemical in said chemical packet;
   volatilizing at least a portion of said chemical; and
   releasing said volatilized chemical into an ambient.

* * * * *